(12) United States Patent
Kneifel et al.

(10) Patent No.: US 6,793,663 B2
(45) Date of Patent: Sep. 21, 2004

(54) SURGICAL APPLICATOR TIP FOR DELIVERING CLIPS OF CLAMPS

(75) Inventors: Bernhard Kneifel, Hagenbach (DE); Günter Herrmann, Grünstadt (DE)

(73) Assignee: Forschungszentrum Karlsruhe GmbH, Karlsruhe (DE)

( * ) Notice: Subject to any disclaimer, the term of this patent is extended or adjusted under 35 U.S.C. 154(b) by 265 days.

(21) Appl. No.: 10/059,517

(22) Filed: Jan. 29, 2002

(65) Prior Publication Data

US 2002/0065535 A1 May 30, 2002

Related U.S. Application Data

(63) Continuation-in-part of application No. PCT/EP00/06110, filed on Jun. 30, 2000.

(30) Foreign Application Priority Data

Jul. 30, 1999 (DE) .......................................... 199 35 904

(51) Int. Cl.[7] .............................................. A61B 17/10
(52) U.S. Cl. ...................................... 606/143; 606/219
(58) Field of Search ................................. 606/142, 143, 606/213, 219, 220, 221, 153–159; 227/175.1, 176.1, 177.1, 901, 902

(56) References Cited

U.S. PATENT DOCUMENTS

| | | | | |
|---|---|---|---|---|
| 3,082,426 A | | 3/1963 | Miles | |
| 4,887,756 A | * | 12/1989 | Puchy | 227/19 |
| 5,258,010 A | * | 11/1993 | Green et al. | 606/219 |
| 5,915,615 A | | 6/1999 | Bauer | |
| 5,951,574 A | * | 9/1999 | Stefanchik et al. | 606/143 |
| 6,010,513 A | * | 1/2000 | Tormala et al. | 606/142 |
| 6,277,131 B1 | * | 8/2001 | Kalikow | 606/143 |
| 6,352,541 B1 | * | 3/2002 | Kienzle et al. | 606/143 |
| 2003/0009177 A1 | * | 1/2003 | Middleman et al. | 606/127 |

FOREIGN PATENT DOCUMENTS

| | | |
|---|---|---|
| EP | 0 094 752 | 11/1983 |
| EP | 0 592 244 | 4/1994 |
| WO | WO 87/04063 | 7/1987 |

* cited by examiner

Primary Examiner—David O. Reip
Assistant Examiner—Jessica R. Baxter
(74) Attorney, Agent, or Firm—Klaus J. Bach

(57) ABSTRACT

In a surgical applicator tip for delivering clips used for connecting tissues, the applicator tip includes a magazine chamber, which receives a magazine with clips having tissue engagement claws and an operating mechanism by which the clips can be removed from the magazine and supplied to the front end of the applicator such that the claws project forwardly therefrom the applicator tip for piercing and engaging tissue parts. Each clip includes a shoulder with an elbow lever structure which, with the tissue pierced by the claws, is pushed against the shoulder whereby the claws are tilted toward each other for firmly holding the tissue parts in contact with each other.

7 Claims, 3 Drawing Sheets

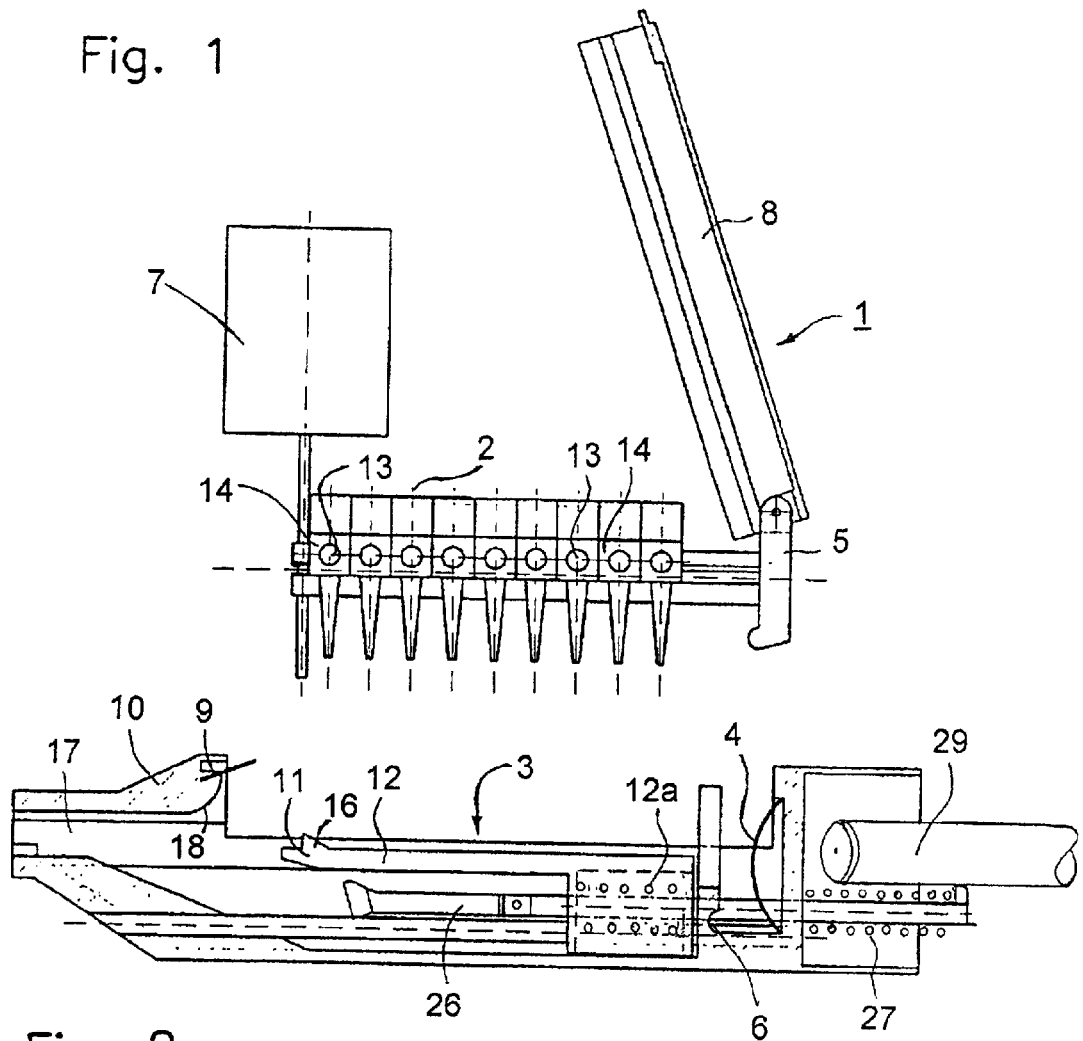
Fig. 1
Fig. 2
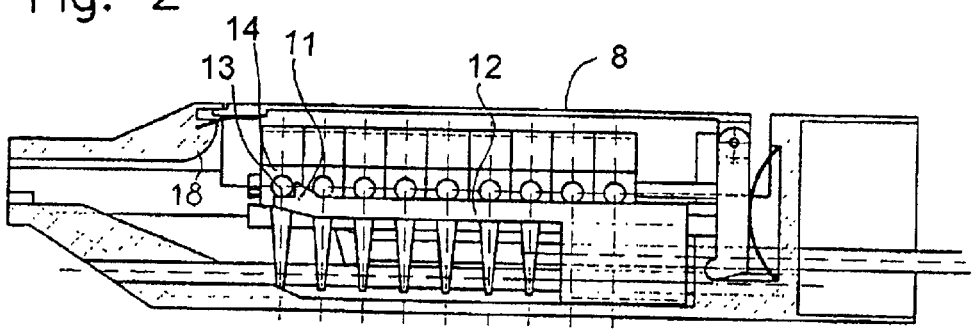
Fig. 3

SURGICAL APPLICATOR TIP FOR DELIVERING CLIPS OF CLAMPS

This is a Continuation-In-Part application of international application PCT/EP00/06110 filed Jun. 30, 2000 and claiming the priority of German application 199 35 904.0 filed Jul. 30, 1999.

BACKGROUND OF THE INVENTION

The invention relates to a surgical applicator tip for the setting of clips and clamps for connecting tissue during minimal invasive surgery.

Minimal invasive surgery equipment permits the performance minimal invasive surgery without the need for large cuts and without the formation of visible scars. Tissue parts are connected internally by clips or clamps using an applicator. Such equipment is used for example for surgery in case of fractures wherein stabilizing screens are connected to the tissue. Presently clips of titanium are used which cannot be decomposed biologically so that they remain in the body. Sometimes it is necessary to remove the titanium clips at a later date if they cause discomfort or pain. It is desirable to employ for the tissue connection clips of a material which provides for the necessary mechanical connection during the healing period of the wound but which, over an extended period, is fully disintegrated by the body by resorption.

Such clips are provided with claws which are closed like tongs by an application of a force and which then remain in the closed position. To handle and operate the clips, an applicator is needed by which the clips can be introduced into the body and set in a simple operating procedure.

It is therefore the object of the present invention to provide a surgical applicator with a tip for delivering and remotely setting clips or clamps in such a way that, on one hand, a sufficient number of clips or clamps can be stored in the applicator and, on the other hand, the clamps can be easily taken from the storage and brought into proper position for clamping.

SUMMARY OF THE INVENTION

In a surgical applicator tip for delivering clips used for connecting tissues, the applicator tip includes a magazine chamber, which receives a magazine with clips having tissue engagement claws and an operating mechanism by which the clips can be removed from the magazine and supplied to the front end of the applicator such that the claws project forwardly therefrom the applicator tip for piercing and engaging tissue parts. Each clip includes a shoulder with an elbow lever structure which, with the tissue pierced by the claws, is pushed against the shoulder whereby the claws are tilted toward each other for firmly holding the tissue parts in contact with each other.

Basically, the applicator comprises three main components: an operating handle, a connecting tube and an applicator tip. The operating handle serves to hold the applicator and includes means for controlling rotation and pivoting of the applicator tip as well as means for releasing and closing the clips. The connecting tube, which is extends between the operating handle and the applicator tip, includes actuating elements for operating the applicator tip which is disposed at the distal end of the connecting tube. The applicator tip includes a magazine for storing a number of clips, means for moving the clips and means for causing the clips to pierce the tissue and for closing the clips. The applicator is received for example in a trocar, which extends for example through a belly and seals the belly space, which is under pressure.

With the design of the applicator tip according to the invention, the clips are handled in a simple and efficient manner. The applicator tip accommodates the clips and the peripheral operating mechanism. The applicator tip is furthermore rotatably and pivotally supported. The clips have a particular shape: They are U-shaped with claw-like legs and are disposed on a storage bar supported by their shoulder portions. The shoulder portion are normally straight and are provided with elbow lever structures. The front clip is engaged by a stop provided at the free end of the storage bar. The subsequent clips are biased forwardly by a spring so that, upon removal of the front clips, the remaining clips move up. The storage or magazine bar is anchored at its rear end to a base plate by which a magazine lid is pivotally supported. The base plate is anchored in a recess upon insertion into the magazine cavity and is held in position by a spring force.

Below the stored clips, an axial movement mechanism is disposed comprising two plungers, that is, a transport and a closing plunger. Both are operated axially by an actuating wire extending through the applicator shaft to an operating mechanism in the operating handle. During forward movement, the closing plunger is first moved along with the transport plunger which engages the front clip of the clip magazine and carries it to the front end of the applicator tip, while, at the same time, pivoting it by 90° to properly position it for installation at the applicator tips opening. There, the clip is held in position, while, at the same time, the closing plunger guided by way of a ramp abuts the elbow lever structure at its elbow joint.

In certain advantageous embodiments, the magazine lid may also cover the applicator tip. With a slight axial movement the lid is engaged in a locking recess in the wall of the applicator tip and is retained in this locked position by the force of a spring.

When the transport plunger is advanced below the clips suspended in the magazine it engages in the process with its two projecting prongs the front clip at cylindrical shoulder projections thereof.

The clip is moved through a guide groove in which the clip, when pivoted by 90°, is guided and which includes a spring structure, which prevents return movement of the clip.

When the clip has arrived at the end opening of the applicator tip, it is first retained in position by a retaining clamp until its claws are pressed into the tissue by the advancing closing plunger. When the claws are disposed within the tissue and the closing plunger is further advanced, the elbow lever structure is moved to a straight end position adjacent the shoulder of the clip, whereby the clip is closed.

The applicator tip includes a magazine chamber in which a sufficiently large number of clips are supported adjacent one another on the storage bar. The transport and closing mechanism is operated by a drive mechanism, which is simple in design and therefore reliable in operation. The shape of the interior of the applicator tip provides for proper guiding and final positioning of the clips for their accurate setting in the tissue parts to be joined.

The applicator tip and the clips will be described below as to their design and operation in greater detail on the basis of the accompanying drawings.

BRIEF DESCRIPTION OF THE DRAWINGS

FIG. 1 shows the magazine for storing clips,

FIG. 2 shows the empty applicator tip with the operating mechanism,

FIG. 3 shows the applicator tip with the clip magazine disposed in the magazine chamber of the applicator tip.

DESCRIPTION OF AN EMBODIMENT OF THE INVENTION

Preparation of the Applicator

Figure 4:
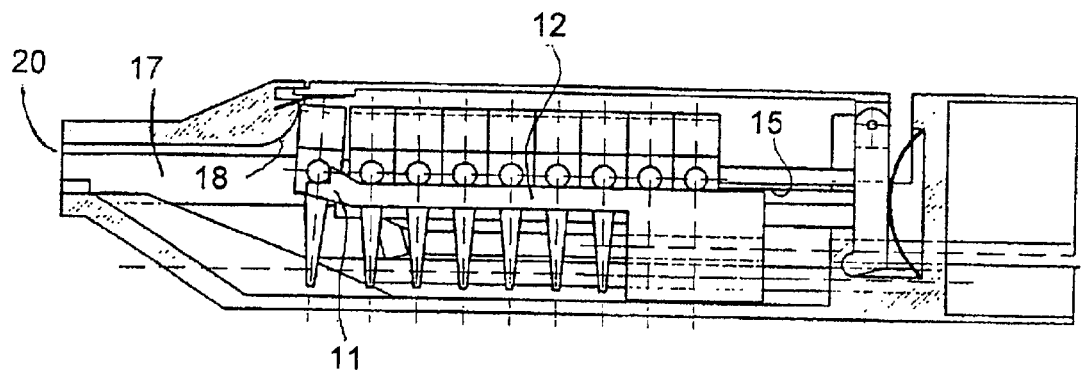
FIG. 4 shows the applicator tip with the transport plunger in a position, in which it is about to engage the clip.
Figure 5:
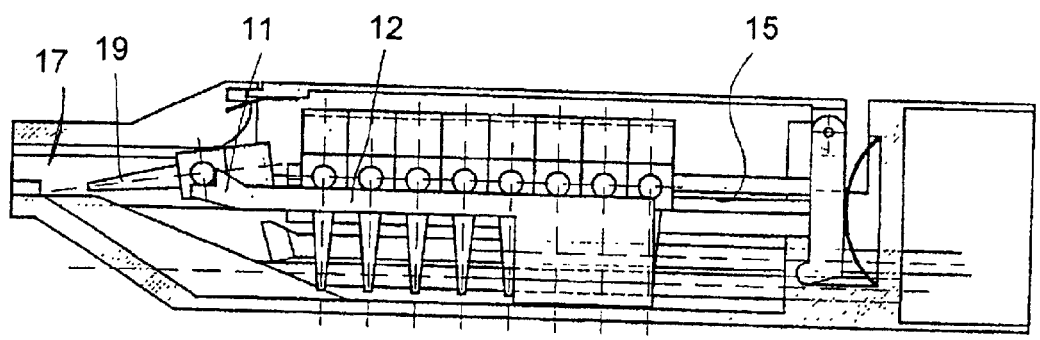
FIG. 5 shows the transfer of the clip.

The magazine 1, filled with clips 2 (FIG. 1), is inserted into the magazine chamber 3 (FIG. 2) of the applicator tip until it is properly disposed therein. When the magazine is properly positioned, a locking lever or end wall 5 is pressed, by a curved leaf spring 4, into the engagement recess 6. Then the transport safety front cover 7 (FIG. 1) is pulled and the magazine lid 8 is closed (FIG. 3). With a slight axial forward movement, the lid 8 is engaged in the groove 9 of the end wall 10 of the applicator tip.

Figure 8:
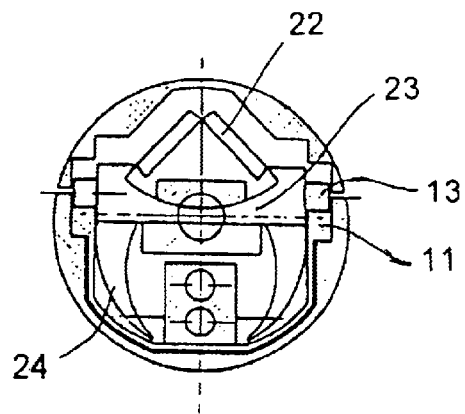
FIG. 8 is a view of the clip as disposed in the front opening of the applicator tip.

After the installation of the magazine, the clips 2 are supported in the magazine adjacent one another (FIGS. 1, 3 and 8). The two prongs 11 with the projections 16 of the transport plunger 12 engage the cylindrical projections 13 at the shoulders 14 of the first clip 2 in the magazine 1 (FIG. 4) and begin to lift the first clip 2 off its seat. The clips in the magazine are under spring tension and are prevented from being released by a clamping or engagement edge at the free end of the support bar 15. The clip is now removed by the transport plunger 12 from the support bar and, while being moved into the guide groove 17, is tilted by 90° by the curved portion 18 of the wall 10 below the locking groove 9 for the magazine lid 8.

During the movement of the clip out of the magazine 1, the clip 2 is held at its sides by the two cylindrical projections 13 on its shoulders 14 in guide grooves such that it moves through the surrounding housing in a controlled manner with the clip claws 19 projecting forwardly.

Figure 6:
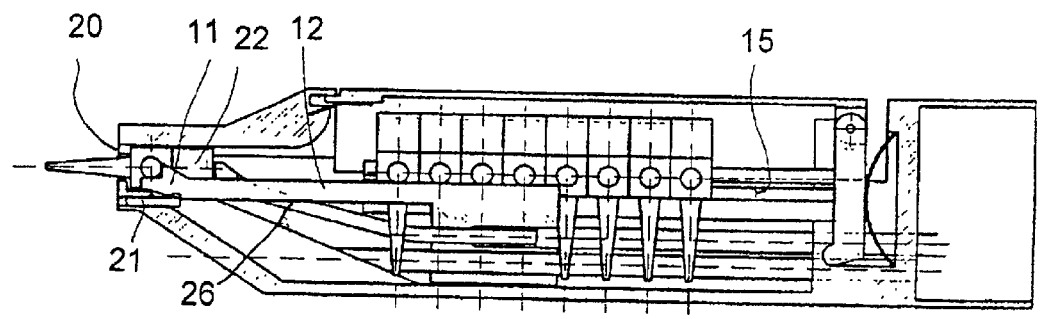
FIG. 6 shows the applicator with the clip positioned at the front opening of the applicator.

Further forward movement of the transport plunger 12 moves the clip 2 past guide springs to the open end 20 of the applicator tip. The guide springs prevent a reverse sliding of the clip. At the open end 20 of the applicator tip, there are retaining clamps 21 (FIGS. 6, 7), which prevent the clip from falling out of its end position before it is inserted into the tissue. When the clip 2 engages the retaining clamps 21, which form a stop, the transport plunger 12 has reached its axial end position. The transport plunger 12 is connected to the operating wire or rather the closing plunger 26 by way of a spring 12a, so that further movement of the operating wire is not transferred to the transport plunger 12 beyond the final end position of the transport plunger 12, but the transport plunger 12 is merely held in engagement with the clip 2 at the front end of the applicator tip.

In this position, the handgrip 22 at the operating handle is not further pulled, but is left in place.

The applicator tip is now moved to a desired position adjacent the tissue to be joined. When properly positioned, the claws of the clip are pushed into the adjacent tissue, in the case of a hernia operation for example through a screen into the upper tissue layer.

At this point, the claws of the clips have only entered the tissue. The clip is still held in the applicator tip. If the handgrip 28 in the handle 25 is now further pulled (FIG. 7), the elbow lever structure 22 of the clip 2 is pushed in by the closing plunger 26. As a result, the shoulder 23 of the clip 2 is curved via joints which couple the elbow lever structure 22 with the shoulder web 23 whereby the tips of the claws 24 are moved toward each other and the clip 2 closes around the penetrated tissue.

Figure 7:
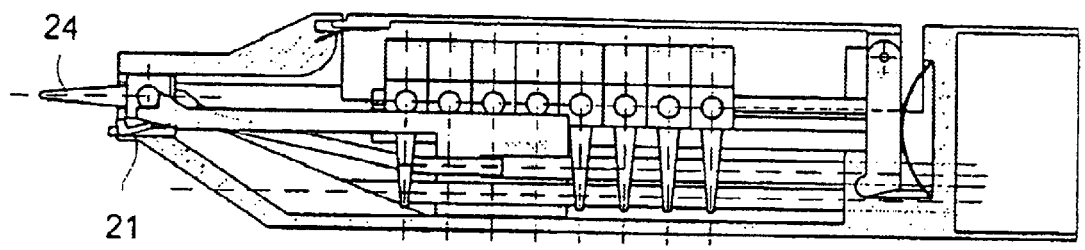
FIG. 7 shows the clip in the position as shown in FIG. 6 with the elbow lever structures engaged by the closing plunger for closing the clip.

When the handgrip 22 is pulled to its end position, the retaining clamp 21 is tilted away and releases the clip 2. The applicator tip can then be pulled back (FIG. 7).

Figure 9:
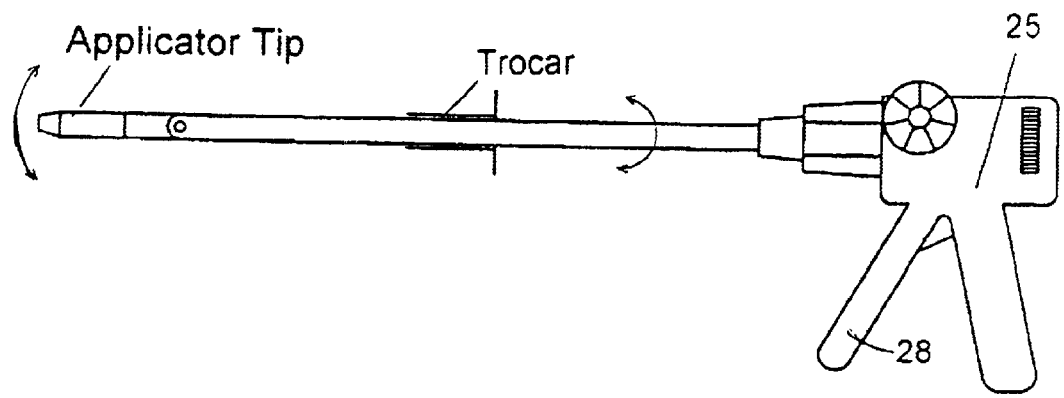
FIG. 9 shows the whole applicator.

When the handgrip 22 at the operating handle 25 of the applicator (FIG. 9) is released, the operating wire 29 with the two plungers is pulled back by the force of the spring 27 to the initial position. The two prongs 11 of the transport plunger 12 lift the front clip 2 so that the prongs 11 can move behind the cylindrical projection 13. A magazine spring structure prevents backward movement of the clips 2 on the clip support bar 15. The arrangement is then again in a position to begin the installation process for the next clip 2 as shown in FIG. 3.

What is claimed is:

1. A surgical applicator tip for delivering clips for joining tissue parts, said applicator tip comprising an applicator tip housing having a magazine chamber, a magazine for containing clips disposed in said magazine chamber, and an operating mechanism for successively removing clips from said magazine for installation in tissue parts, each of said clips including a shoulder portion and curved claws projecting from said shoulder portion at opposite ends thereof, and an elbow lever structure disposed on, and connected to, said shoulder portion at said opposite ends thereof so that the free ends of said claws move toward each other when said elbow lever structure is straightened, said clips being supported with their shoulder portions on a support bar one adjacent the other and being biased toward the front end of said applicator tip, said magazine having a front cover which is removable after insertion of said magazine into said magazine chamber for releasing said clips and a pivotably supported magazine lid with a projection extending springbiased into a recess in said applicator tip when said magazine is disposed in said magazine chamber for retaining said magazine in said magazine chamber, said applicator tip further including a transport plunger for moving said clips and a closing plunger for engaging said elbow lever structure for closing said clips, both said plungers being operated from a handle of said surgical applicator by way of an operating wire, said transport plunger having engagement prongs for engaging a front clip and moving it toward the front end of said applicator tip while pivoting said clip about 90° so that the claws of said clip project forwardly from said applicator tip and said closing plunger is then movable into engagement with the side of said shoulder opposite said claws for engaging said elbow lever structure with a sufficient force to straighten said elbow lever structure thereby causing the claws to move toward each other for firmly retaining tissue portions engaged therebetween.

2. A surgical applicator tip according to claim 1, wherein said magazine chamber has a front end wall which is rounded for guiding said clip from a storage position, in which said claws extend normal to the direction of movement, to said 90° pivoted position, in which said claws project forwardly for movement of said clip to the front end of said applicator tip.

3. A surgical applicator tip according to claim 2, wherein said front end wall includes a recess and said magazine includes a pivotable lid with a lip received in said recess when said magazine is disposed in said magazine chamber for locking said lid in a closed position and retaining said magazine in said magazine chamber.

4. A surgical applicator tip according to claim 3, wherein said transport plunger includes prongs at its front end and said clips include projections at opposite ends of said shoulders, said prongs including engagement recesses for engaging said projections of said clips and moving said clips to the front end of said applicator tip.

5. A surgical applicator tip according to claim 4, wherein said applicator tip includes a guide channel for guiding said clips to the front end of said applicator tip and said guide channel includes spring guide means permitting forward movement of said clips but preventing backward movement of said clips.

6. A surgical applicator tip according to claim 5, wherein, at its front, said guide channel includes at least one retaining clamps which holds a clip moved to the front end of said application tip in position with its claws projecting from said applicator tip.

7. A surgical applicator tip according to claim 6, wherein a ramp surface is provided at the front end of said magazine chamber so as to lead upwardly to said guide channel for leading said closing plunger into said guide channel behind said clip for actuating said elbow lever structure to close said clip.

* * * * *